United States Patent [19]

Prino et al.

[11] Patent Number: 4,693,995
[45] Date of Patent: Sep. 15, 1987

[54] PHARMACEUTICAL COMPOSITION FOR THE TREATMENT OF ACUTE MYOCARDIAL ISCHEMIA

[75] Inventors: Giuseppe Prino, Milan; Marisa Mantovani, Villa Guardia Como; Riccardo Niada, Varese, all of Italy

[73] Assignee: Crinos Industria Farmacobiologica S.p.A., Como, Italy

[21] Appl. No.: 701,695

[22] Filed: Feb. 14, 1985

[30] Foreign Application Priority Data

Feb. 16, 1984 [IT] Italy ............................... 19645 A/84

[51] Int. Cl.$^4$ ............................................. A61K 31/70
[52] U.S. Cl. ...................................................... 514/44
[58] Field of Search ............... 424/95; 514/44; 536/24

[56] References Cited

U.S. PATENT DOCUMENTS

| | | | |
|---|---|---|---|
| 3,770,720 | 11/1973 | Butti et al. | 536/24 |
| 3,829,567 | 8/1974 | Butti et al. | 514/44 |
| 3,899,481 | 8/1975 | Butti et al. | 536/28 |

OTHER PUBLICATIONS

Prostaglandis 16, 885–889, 1978.
Thromboxane and Prostacyclin Release from Ischaemic Myocardium in Relation to Arrhythias, Susan Coker, et al.
Prostogandis, Nov., 1979, vol. 18, No. 5, The Actions on Prostaglandis I$_1$ and I$_2$ on Arrhythmias Produced by Coronary Occlusion in the Rat or Dog, T. L. S. Wu, pp. 707–720.
European Journal of Pharmacology, 56 (1979) 95–103, Studies on the Protective Effect of Prostacyclin in Acute Myocardial Ischemia, Martin L. Ogletree.
Antithrombotic Activity of Polydeoxyribonucleotides of Mammalian Orgin (Laboratory Code: Fraction P) in Experimental Animals, R. Niada, et al.
Thrombosis Research 30: 1–11, 1983; Pharmacokinetics of Defibrotide and its Profibrinolytic Activity in the Rabbit, R. Pescador, et al.
The American Journal of Cardiology, Dec. 1969, vol. 24, No. 6, Early Phase of Myocardial Ischemic Injury and Infarction, Robert B. Jennings, M.D.
American Association of Pathologists, pp. 241–255, Lethal Myocardial Ischemic Injury, Robert B. Jennings, M.D. et al.
Thrombosis Research 30: 1–11, 1983, Pharmacokinetics of Defibrotide and its Profibrinolytic Activity in the Rabbit, R. Pescador, et al.
Chem. Abst., 98; 27621p, Niada et al., 1983.
Chem. Abst., 97; 207977x, Cuccheri, et al., 1982.
Chem. Abst., 98; 191280x, Pescador et al., 1983.
Chem. Abst., 102; 119683q, Ulutin et al., 1985.
Chem. Abst., 103; 399g, Niada et al., 1985.

*Primary Examiner*—Johnnie R. Brown
*Assistant Examiner*—John W. Rollins, Jr.
*Attorney, Agent, or Firm*—McAulay, Fields, Fisher, Goldstein & Nissen

[57] ABSTRACT

Defibrotide, a polydeoxyribonucleotide, obtained by extraction from animal organs, is the active ingredient of compositions for the treatment of acute states of myocardial ischemia and infarction.

5 Claims, No Drawings

PHARMACEUTICAL COMPOSITION FOR THE TREATMENT OF ACUTE MYOCARDIAL ISCHEMIA

FIELD OF THE INVENTION

The present invention relates to a pharmaceutical composition useful for the prevention and the treatment of acute pathological states of the myocardium, such as acute ischemia, with or without necrosis of the myocardium (acute infarction).

BACKGROUND OF THE INVENTION

The pathogenetic mechanisms of the acute myocardial infarction are not yet fully understood. In recent years the role of the coronaryc spasm in the pathogenesis of some forms of angina has been reevaluated and the hypothesis has been suggested that the acute myocardial infarction might in some cases be caused by an extended coronary spasm possibly followed, downstream of the functional stenosis, by alterations of the blood flow and of the vascular wall, with stasis and subsequent platelet aggregation, release of tromboxane ($T \times A_2$) and then thrombosis.

The $T \times A_2$ may potentiate the vasospastic phenomenon which can be extended to other areas, thus involving potential vessels forming part of the side circulation.

To date, for the treatment of the myocardial ischemia and infarction, some therapeutical proposals have been brought forward and/or practiced, based on the use of:
coronary vasodilators, nitrates
beta-blocking compounds
calcium-antagonizing substances
prostacycline The nitroderivatives are vasodilating compounds which act directly on all the vessels; the vasodilation as induced by these drugs on the side circulation might cause the intramyocardial blood flow to be redistributed in the presence of a coronary occlusion. In some experimental work nitroglycerin has been able to reduce the myocardial ischemia or infarction, but other workers did not found significant effects with nitroglycerin.

Rather recent clinical studies indicated that nitroglycerin, upon being intravenously injected, may increase the incidence of arrhytmias without modifying the infarction.

Propranolol and the novel cardioselective beta-blocking compounds (Atenolol, Practolol, Metoprolol) have been used with the purpose of reducing the damage caused by the myocardial infarction.

Some authors demonstrated in a dog afflicted with occlusion of the circumflex coronary arteria that Propranolol caused the necrosis to be significantly reduced.

More recent studies, however, did not show significant effects for Propranolol.

Practolol demonstrated effects more interesting than Propranolol in the treatment of the myocardial ischemia, in a comparison study carried out in dogs by evaluating haemodynamic parameters, the oxygen consumption of the myocardium, lactate.

The action of these drugs may be probably attributed to a reduction of the oxygen consumption of the myocardium, as a consequence of the blocking of the sympathic stimulation on the cardiac frequence and contractility.

The calcium antagonizing drugs (Verapamil, Nifedipine, and others), cause the calcium channels to be blocked, and the tone of the vascular smooth muscles to be reduced whereby a coronary but also systemic vasodilation is induced, moreover the blocking of the calcium flow causes the myocardial contractility and oxygen consumption to be reduced. Some authors found in dogs with occlusion of the circumflex coronary arteria a modest but significant reduction of the necrosis after pretreatment with Verapamil; at higher dosages the drug had hypotensive effects and induced a cardiac blocking of various grades. The results obtained with Nifedipine are rather controversial. Nifedipine at high dosages causes a reduction in dogs of aortic pressure, an increase of the cardiac frequency and an increase of the ischemic area; at low dosages it induces a lower pressure diminution and a slight reduction of the ischemic area.

The anti-ischemia effects of Fendiline (negative chronotropic action, increase of the coronary flow) and of Felodipine (preventing action on the ventricle fibrillation induced by the occlusion of the descending coronary in the pig) have been recently described.

The anti-arrhytmic action of Lidocaine, prevailingly attributed to direct electrophysiological effects, is especially interesting in the treatment of ventricular arrhytmias associated with a sympathetic hyperactivity.

Lidocaine, when intravenously injected, reduces the cardial sympathetic activity, this effect would be caused by a central action of the drug.

The Dipyridamole has a dilating action particularly on the coronary small arteriae; this drug is moreover able to interfere with the platelet functionality by potentiating the prostacycline effect or by inhibiting the phosphodiesterases, whereby the intracellular cAMP is increased.

Dipyridamole has induced, under some experimental conditions, an increase of the coronary haematic flow and a reduction of the ischemic area in dogs with occluded coronary artery.

These effects of Dipiridamole are however not evident when the drug gives place to relevant pressure reduction.

Sulfinpyrazone does inhibit the platelet aggregation and the biosynthesis of prostaglandins; this drug has reduced the ventricular arrhytmias and the incidence of the fibrillation in cats with occluded descending coronary. The extension of the ischemic area induced by the occlusion of the coronary however was not reduced by treatment with Sulfinpyrazone.

It has been recently proposed to use prostacyclin ($PGI_2$) for the treatment of the myocardial acute infarction. $PGI_2$ was found to be active in the reducing the arrhytmias occurring in the early post-infarction phases in dogs and in rats after ligation of the coronary artery: Harvie C. J. et al; "The action of prostaglandin $E_2$ and $F_{1\alpha}$ on myocardial ischaemia-infarction arrhytmias in the dog".

Prostaglandis 16, 885–899, 1978; Cocker S. J. et al, "Thromoboxane and prostacyclin release from ischaemic myocardium in relation to arrhytmias". Nature, 291, 323–324, 1981 and Au T. L. S. et al "The actions of prostaglandins $I_2$ and $E_2$ on arrhythmias procured by coronary occlusion in the rat and dog". Prostaglandins, 18 707–720, 1979).

In a study of the protective effect of $PGI_2$ on the acute mycoardial ischemia induced in the cat, the hypothesis was made that $PGI_2$, administered by perfusion, does protect the ischemic myocardium by reducing the oxygen demand of the tissue, through a reduction of the cardiac work and, probably, by inhibiting the platelet aggregation and by preserving the integrity of the myocardial cells (Ogletree M. L. et al, "Studies on the protective effect of prostacyclin in acute myocardial ischemia". Eur. J. Pharmacol., 56 95–103, 1979).

From the above therapeutical picture, which has been necessarily reported in a very condensed manner, it is clear that the problem of the treatment of the myocardial infarction and ischemia has not found to date a therapeutically satisfactory solution.

SUMMARY OF THE INVENTION

It has been now found and is the subject of the present invention that the above identified therapeutical problem is essentially solved by means of a therapeutical composition which is characterized by containing, as the active ingredient, the substance called Defibrotide, i.e. a polydeoxyribonucleotide obtained by extraction from animal organs.

Defibrotide (DCI, liste 21, Chronique OMS, 35, 5 suppl. 4 (1981), is as above stated a polydeoxyribonucleotide (U.S. Pat. No. 3,829,567), obtained through extraction from animal organs (see U.S. Pat. Nos. 3,770,720 and 3,899,481 to which reference is made for greater details), which is devoid of anticoagulating activity and of haemodynamic effects, showing relevant profibrinolytic and anti-thrombotic activity under different experimental conditions (Niada R. et al. "Antithrombotic activity of polydeoxyribonucleotides of mammalian origin (Laboratory Code: Fraction P) in experimental animals", VII International Congress on Thrombosis and Haemostasis (London 15–20 July 1979) Abs. No. 1162, Thrombosis and Haemostasis, 42, 474, 1979 and Pescador R. et al. "Pharmacokinetics of Defibrotide and of its profibrinolytic activity in the rabbit'-'—Thrombosis Research, 30, 1–11, 1983).

It is particularly worth to mention that, as confirmed by the several studies published on Debifrotide, this active principle is practically devoid of toxicity as well as from objectionable side effects.

It is also worth to mention that to date Defibrotide has found or is finding therapeutical use for pathologies which are essentially different from those contemplated by the present invention.

In fact Defibrotide is indicated as antithromobotic drug, for the treatment of peripheral arteriopathies and for the care of states of acute renal insufficiency. These uses might not obviously suggest the results achieved by the present invention, namely to provide a therapeutical means effective for the treatment of cases of myocardial acute ischemia and infarction which, as it can be appreciated from the previously mentioned situation, did not found to date an effective remedy.

As it will be detailedly illustrated hereinafter, Defibrotide has been tested in a model of lethal acute myocardial ischemia in the cat with total occlusion of the descending coronary arthery at its origin; the drug was injected in the vein (bolus injection followed by perfusion), after the occlusion upon the appearance of significant electrocardiographic alterations.

Defibrotide, surprisingly, has been capable of reducing the electrocardiographic alterations, of bringing to the normality the rate of creatine-phosphokinase in the myocardium and of protecting from death all the treated animals. In the corresponding control group the death rate was 80%.

More specifically it has been selected the model of ischemia induced by ligation of the left descending coronary artery in the cat, according to the indications of Jennings (Jennings R. B., "Early phase of myocardial ischemic injury and infarction. "Am. J. Cardiology, 24, 6 753–765, 1969; Jennings R. B. et al. "Lethal myocardial ischemic injury." Am. J. Path., 102, 2, 241–255, 1981).

According to this model the ligation, applied at the origin of the coronary artery, induces heavy electrocardiographic alterations (raising of the ST tract) as well as of haemodynamic and enzimatic nature, such as to cause the death of the animal (owing to ventricular fibrillation) in 12 of the 15 cats of the control group within the first 15 to 30 minutes after the occlusion.

Defibrotide has been injected intravenously at the dose of 32 mg/kg as a "bolus" followed by perfusion of 32 mg/kg/hour, one minute after the coronary occlusion, when evident electrocardiographic alterations appear.

All the animals treated with Defibrotide (10 cats) were protected from death during all the experiment duration (6 hours).

The protecting effect of the drug has been also evaluated on the average aortic pressure and on the cardiac frequency; the values of these parameters, reduced in the early phases of the ischemia, have been significantly restored to the normal levels.

The PRI index (average aortic pressure times cardiac frequency) which does indirectly indicate oxygen consumption of the myocardial tissue, was increased by 50%, with respect to the control, in the animals treated with Defibrotide.

The increase of creatine phosphokinase (CPK) in the plasma and its marked reduction in the ischemic tissue are modifications fully antagonized by the Defibrotide. According to this model also the effect of some known drugs, such as Trinitroglycerin (10 μg/kg plus 300 μg/kg/hour i.v.), Lidocaine (2 μg/kg plus 6 μg/kg/hour i.v.), Atenolol (3 μg/kg plus 9 μg/kg/hour i.v.) Sulfinpyrazone (32 μg/kg plus 32 μg/kg/hour i.v.) Verapamil (1 μg/kg plus 3 μg/kg/hour i.v.) and Prostacyclin (30 or 60 nM/kg plus 30 or 60 nM/kg/hour i.v. or by intracardiac perfusion) has been tested; all these drugs, under the above experimental conditions, did not protect the treated animals from death. Only trinitroglycerin delayed the death time by about 2 hours, but no modification appeared as regards the haemodynamic and enzimatic parameters.

Consequently the capacity of Defibrotide of protecting from death all the cats affected by infraction under the same experimental conditions in which prostacyclin was ineffective is surprising.

In Table I the more significant results obtained in the model of lethal ischemia are reported.

These data indicate a therapeutical action of Defibrotide in the subject model of myocardial ischemia. Defibrotide injected intravenously (bolus injection followed by perfusion) after inducing the lethal ischemia, protected from death all the treated animals, restoring to normal levels the tested haemodynamic parameters and the values of creatine phosphokinase in the plasma and in the ischemic tissue.

The tested known drugs did not protect the animals from death and no modification was detected as regards the haemodynamic parameters.

TABLE 1

Effect of Defibrotide, Trinitroglycerin, Lidocaine, Atenolol, Sulfinpyrazone, Verapamil and Prostacyclin on the survival, on the death time and on the creatine phosphokinase (CPK) of the myocardium in the lethal ischemia (AMI) induced by the occlusion of the coronary artery in the cat.

| Treatment | survival | death time (minutes) | myocardial CPK (I.U./mg proteins) right ventricle (control) | left ventricle (ischemic) |
|---|---|---|---|---|
| SHAM (control) | 10/10 | — | 14,51 ± 1,11 (10) | 14,67 ± 79° (10) |
| Sol. (AMI) | 3/15 | 21,7 ± 5,7 (12) | 12,69 ± 0,24 (3) | 2,46 ± 0,71+ (3) |
| Defibrotide (AMI) 32 mg/kg + 32 mg/kg h | 10/10 | — | 13,67 ± 1,38 (10) | 14,24 ± 1,36° (10) |
| Trinitroglycerin (AMI) 10 μg/kg + 300 μg/kg h | 0/7 | 89,0 ± 19,7* (7) | — | — |
| Lidocaine (AMI) 2 mg/kg + 6 mg/kg h | 0/7 | 47,7 ± 20,1** (7) | — | — |
| Atenolol (AMI) 3 mg/kg + 9 mg/kg h | 0/7 | 35,6 ± 10,9** (7) | — | — |
| Sulfinpyrazone (AMI) 32 mg/kg + 32 mg/kg h | 0/7 | 35,3 ± 12,6** (7) | — | — |
| Verapamil (AMI) 1 mg/kg + 3 mg/kg h | 0/7 | 45,0 ± 15,6** (7) | — | — |
| Prostacyclin (AMI) 30-60 nM/kg + 30-60 nM/kg h | 0/5 | 10,8 ± 5,6** (5) | — | — |

Death time: *P 0.001 vs. physiolog. solution (AMI)
**N.S. vs. physiolog. solution (AMI)
CPK left ventricle: +P 0,001 vs. right ventricle °N.S. vs. right ventricle
In brackets the number of data.

Likewise, the experimental evaluation was carried out of the action of Defibrotide in the case of non lethal myocardial infarction.

According to the method of Jennings (Jennings R. B. et al. "Lethal myocardial ischemic injury." Am. J. Path., 102, 2, 241-255, 1981) and Oglotree ((Oglotree M. L. et al "Studies on the protective effect of prostacyclin in acute myocardial ischemia".

European J. Pharmcol. 56, 95-103, 1979) the model of ischemia was selected which is induced by the ligation of the left descending coronary arteria in the cat.

In this model the ligation, applied at 12 to 14 mm from the origin of the coronary, caused the death of the animal only in a few cases which were discarged from this study; the ischemia induced by this occlusion gives place to serious electrocardiographic alterations (raising of the ST tract) and to relevant haemodynamic and biochemical alterations. The following parameters were examined: electrocardiogram, aortic pressure cardiac frequency, PRI, creatine phosphokinase (CPK) in the plasma and CPK, lactate and ATP in the myocardial tissue.

Defibrotide was perfused intravenously at the dose of 32 mg/kg/hour three hours before the ligation of the coronary and the perfusion was maintained for the whole period of the occlusion (5 hours). The drug was capable of significantly reduce the electracardiographic alteration (raising of the ST tract), of restoring the haemodynamic parameters and the CPK levels in the myocardial tissue and in the plasma to the normal values. The lactate increase and the ATP reduction, these modifications having been detected in the ischemic tissue, were fully antagonized by Defibrotide.

In this experimental model only Atenolol was tested among the known drugs.

Atenolol (1 mg/kg/hour u.v.) has shown some protecting effect only on CPK; no modification has been noticed as regards the other tested parameters (both biochemical and haemodynamic).

The pharmaceutical compositions of the present invention can be formulated with techniques, excipients and vehicles of conventional and well known type, for the administration both orally and by injection, particularly by intravenous route. The dosages of active ingredient in the compositions according to the present invention ranges between 50 and 1500 mg for unitary dose, whereas to attain the desired results the daily administration of 12 to 14 mg/kg is suggested.

We claim:

1. A method of testing acute myocardial ischemia in a patient in need of such treatment, comprising administering to said patent a therapeutically effective amount of defibrotide in a pharmaceutically acceptable, inert carrier.

2. The method of claim 1 wherein said defibrotide is administered orally.

3. The method of claim 1 wherein said defibrotide is injected intravenously.

4. The method of claim 1, wherein said defibrotide is administered in unitary doses containing from 50 to 1500 mg thereof.

5. A method of treating acute myocardial ischemia in a patient in need of such treatment, comprising administering to said patient a daily dosage of about 12 mg to about 14 mg per Kg. of body weight.

* * * * *